US008530385B2

(12) United States Patent
Yeritsyan et al.

(10) Patent No.: US 8,530,385 B2
(45) Date of Patent: Sep. 10, 2013

(54) HERBICIDAL FORMULATIONS FOR COMBINATIONS OF DIMETHYLAMINE AND POTASSIUM SALTS OF GLYPHOSATE

(75) Inventors: Karen Yeritsyan, Dunedin (NZ); Timothy Allen Jenkins, Christchurch (NZ)

(73) Assignee: Donaghys Industries Limited, Christchurch (NZ)

(*) Notice: Subject to any disclaimer, the term of this patent is extended or adjusted under 35 U.S.C. 154(b) by 31 days.

(21) Appl. No.: 12/747,625

(22) PCT Filed: Dec. 10, 2008

(86) PCT No.: PCT/NZ2008/000329
§ 371 (c)(1),
(2), (4) Date: Jul. 8, 2010

(87) PCT Pub. No.: WO2009/075591
PCT Pub. Date: Jun. 18, 2009

(65) Prior Publication Data
US 2010/0279867 A1 Nov. 4, 2010

(30) Foreign Application Priority Data

Dec. 13, 2007 (NZ) ........................................ 242910
Dec. 13, 2007 (NZ) ........................................ 564282

(51) Int. Cl.
*A01N 57/00* (2006.01)

(52) U.S. Cl.
USPC ........................................................ 504/127

(58) Field of Classification Search
None
See application file for complete search history.

(56) References Cited

U.S. PATENT DOCUMENTS

| | | | |
|---|---|---|---|
| 3,799,758 A | 3/1974 | Franz | |
| 4,405,531 A | 9/1983 | Franz | |
| 5,750,468 A | 5/1998 | Wright et al. | |
| 6,277,788 B1 | 8/2001 | Wright | |
| 6,451,735 B1 | 9/2002 | Ottaway et al. | |
| 6,479,434 B1 | 11/2002 | Gillespie et al. | |
| 6,544,930 B2 | 4/2003 | Wright | |
| 6,881,707 B2 | 4/2005 | Howat et al. | |
| 7,049,270 B2 | 5/2006 | Lennon et al. | |
| 7,135,437 B2 | 11/2006 | Pallas et al. | |
| 7,316,990 B2 | 1/2008 | Tank et al. | |
| 7,883,715 B2 * | 2/2011 | Abraham et al. | ............ 424/405 |
| 2006/0194699 A1 * | 8/2006 | Moucharafieh et al. | ...... 504/206 |
| 2006/0270556 A1 | 11/2006 | Wright et al. | |
| 2007/0082819 A1 | 4/2007 | Perry et al. | |
| 2009/0018018 A1 | 1/2009 | Gioia et al. | |
| 2009/0062123 A1 | 3/2009 | Quick et al. | |
| 2009/0209425 A1 | 8/2009 | Zhu et al. | |

FOREIGN PATENT DOCUMENTS

| | | |
|---|---|---|
| WO | WO 91/04661 | 4/1991 |
| WO | WO 96/32839 | 10/1996 |
| WO | WO 98/17109 | 4/1999 |
| WO | WO 01/89302 | 11/2001 |
| WO | WO 03/013241 | 2/2003 |
| WO | WO 2005/016002 | 2/2005 |
| WO | WO 2006/096480 | 9/2006 |
| WO | WO 2007/147208 | 12/2007 |
| WO | WO 2009/075588 | 6/2009 |

OTHER PUBLICATIONS

J.L. Flint and M. Barrett, "Effects of Glyphosate Combinations with 2,4-D or Dicamba", *Weed Science* vol. 37, No. 1 Jan. 1989, pp. 12-18.
"Next-Generation Glyphosate from Dow AgroSciences Issued EPA Label Registration", U.S. Agriculture News from Dow AgroSciences, Jul. 17, 2007, 2 pp.
International Search Report issued in corresponding PCT Application No. PCT/NZ2008/000285, mailed Jan. 19, 2009.
International Preliminary Report on Patentability in corresponding PCT Application No. PCT/NZ008/000285, mailed May 13, 2009.
International Preliminary Report on Patentability in corresponding PCT Application No. PCT/NZ008/000329, mailed Jun. 15, 2010.

* cited by examiner

*Primary Examiner* — Alton Pryor
(74) *Attorney, Agent, or Firm* — Greer, Burns & Crain, Ltd.

(57) ABSTRACT

A high strength herbicidal composition including: water; glyphosate, predominantly in the form of a combination of dimethylamine salt and potassium salt, in solution in the water in an amount of about 350 grams or greater of acid equivalent per liter of the composition, wherein the composition is formulated to include dimethylamine in an amount to form a salt with about 5% or greater, by weight, of total glyphosate and to include potassium in an amount to form a salt with a percentage of total glyphosate so that the combined sum of glyphosate in dimethylamine and potassium salts is at least 45% of total glyphosate; and optionally, one or more surfactants and/or one or more humectants.

18 Claims, No Drawings

HERBICIDAL FORMULATIONS FOR COMBINATIONS OF DIMETHYLAMINE AND POTASSIUM SALTS OF GLYPHOSATE

RELATED APPLICATIONS

This application claims the benefit of New Zealand Patent Application No. 564282 filed 13 Dec. 2007, and Australian Patent Application No. 2007242910 filed 13 Dec. 2007, which are incorporated herein by reference in their entirety.

FIELD OF THE INVENTION

The present invention relates to high strength formulations of glyphosate, including the dimethylamine salts of glyphosate, and in particular, formulations comprising the combination of these salts with potassium salts, and methods of use thereof.

BACKGROUND OF THE INVENTION

Glyphosate is a known, effective herbicide. There are several organic ammonium salts of glyphosate useful as herbicides, including the methylamine salt and dimethylamine salt, and, as an example, monoalkylammonium and dialkylammonium (see, e.g., U.S. Pat. No. 4,405,531). Various glyphosate formulations are currently marketed, many of which are aqueous solutions that can be used as is or diluted prior to use.

Typically the glyphosate is provided as a salt that exhibits sufficiently high solubility in water to provide a high strength herbicidal formulation. For example, high strength formulations are known for the isopropylamine salt (IPA), the monoethanolamine (MEA) salt, and various formulations of the potassium (K) salt of glyphosate (see, e.g., U.S. Pat. No. 6,277,788; U.S. Pat. No. 6,365,551; WO 01/89302).

A high strength formulation is desirable for a variety of economic and environmental reasons. For example, it is desirable to provide a high strength formulation to reduce shipping and handling costs and to reduce the amount of packaging material that must be disposed. The high strength formulations are preferably stable and retain potency during storage and shipping. Furthermore, the high strength formulation are optimally provided as a clear, homogeneous liquid that is stable at temperatures at least as high as 50° C. and does not exhibit any precipitation at temperatures as low as 0° C.

However, high strength formulations can result in high viscosity. For example, formulations of the commonly used IPA salt of glyphosate become increasingly viscous at concentrations greater than 350 gram acid equivalent per liter (gae/L), particularly at concentrations greater than 440 gae/L. The high viscosity makes the formulation difficult to measure and pump, especially at the lower temperatures typically encountered at the beginning of the growing season.

The available glyphosate formulations typically include a surfactant. Inclusion of a surfactant can be desirable, as the resulting formulation can exhibit increased herbicidal activity or other improved characteristics. For example, glyphosate formulations are known to include alkylbetaine surfactants in combination with other surfactants (see, e.g., WO 03/067689).

A major limitation of the MEA and K salts of glyphosate is the incompatibility with a wide range of surfactants. In particular, polyoxyethylene alkylamines are only compatible with the MEA salt of glyphosate when the sum of the total average number of carbon atoms plus the average number of oxyethylene groups is equal to or less than 25 (see, e.g., U.S. Pat. No. 6,277,788). Similarly, many common surfactants are not compatible with the glyphosate K salt solution. For example, alkylamine ethoxylate surfactants are only compatible (i.e., allow a homogeneous mixture) when the degree of ethoxylation is no more than about 5, and such surfactants have a higher potential to cause eye irritation.

In addition, certain surfactants can interact with the glyphosate salt to increase the viscosity of the herbicidal formulation. For example, some of the surfactants in the oxyalkylene alkylamine class of compounds, when combined with the glyphosate salt, increase the viscosity of the formulation: If the viscosity is too high, handling of the concentrated herbicide can be difficult. Furthermore, highly viscous liquids are difficult to accurately measure, either for application to the plants or for dilution to a less concentrated spray solution. Depending upon the concentration and specific surfactant, the herbicidal formulation can form a gel, which makes most applications extremely difficult if not impossible to perform.

Dimethylamine is a flammable gas and generally provided as an aqueous solution at concentrations of about 40%. As such, it is difficult to obtain highly concentrated salts of glyphosate using only DMA solution as starting material. In laboratory conditions, the highest concentration of glyphosate prepared as DMA salt has been 560 gae/L (grams acid equivalent per liter), even fully loaded with surfactant.

In light of the above described problems, there is a continuing need for improvements in the relevant field including improved high strength herbicidal formulations that exhibit low viscosity and suitable efficacy. The present invention addresses these needs and provides a wide variety of benefits and advantages.

SUMMARY OF THE INVENTION

It has now been found that the dimethylamine (DMA) salts of glyphosate can be used in combination with potassium (K) salts of glyphosate to allow the preparation of advantageous high strength liquid herbicide formulations.

The present invention encompasses a high strength herbicidal formulation comprising: (a) water, (b) glyphosate, predominantly in the form of the DMA/potassium (DMA/K) salts, in solution in the water in an amount of greater than about 350 gae/L of the composition, and (c) optionally, at least one surfactant and/or humectant.

In certain aspects; the high strength herbicidal formulation of the invention includes a herbicidally efficacious surfactant. This surfactant can be selected to enhance the herbicidal activity of the formulation and to minimize the viscosity of the high strength formulation, or provide other advantages.

In one particular aspect, the invention encompasses a high strength herbicidal composition comprising: (a) water, (b) glyphosate, predominantly in the form of a combination of dimethylamine salt and potassium salt, in solution in the water in an amount of about 350 grams or greater of acid equivalent per liter of the composition, wherein the composition is formulated to include dimethylamine in an amount to form a salt with about 5% or greater, by weight, of total glyphosate and to include potassium in an amount to form a salt with a percentage of total glyphosate so that the combined sum of glyphosate in dimethylamine and potassium salts is at least 45% of total glyphosate, and (c) optionally, one or more surfactants and/or one or more humectants.

In other aspects, the composition is formulated to include dimethylamine in an amount to form a salt with about 20% to about 55%, by weight, of total glyphosate and to include potassium in an amount to form a salt with a percentage of total glyphosate so that the combined sum of glyphosate in dimethylamine and potassium salts is at least 45% of total glyphosate.

In yet other aspects, the composition is formulated to include dimethylamine in an amount to form a salt with about 50%, by weight, of total glyphosate and to include potassium in an amount to form a salt with a percentage of total glyphosate so that the combined sum of glyphosate in dimethylamine and potassium salts is at least 50% of total glyphosate.

In still other aspects, the composition is formulated to include potassium in an amount to form a salt with about 20% to about 95%, by weight, of total glyphosate.

In further aspects, the composition is formulated to include potassium in an amount to form a salt with about 30% to about 80%, by weight, of total glyphosate.

In yet further aspects, the composition is formulated to include potassium in an amount to form a salt with about 50%, by weight, of total glyphosate.

In still further aspects, the composition comprises greater than about 540 grams of acid equivalent of glyphosate per liter of the composition.

In even further aspects, the composition comprises greater than about 560 grams of acid equivalent of glyphosate per liter of the composition.

In yet even further aspects, the composition comprises greater than about 580 grams of acid equivalent of glyphosate per liter of the composition.

In another aspect, the one or more surfactants are selected from the group consisting of alkyl polyglucosides and polymeric quaternary ammonium compounds.

In yet another aspect, the one or more surfactants comprise an alkyl polyglucoside.

In still another aspect, the one or more surfactants comprise a mixture of alkyl polyglucoside and polymeric ammonium quaternary compound in a ratio of about 1:9 to about 9:1.

In even another aspect, the one or more humectants are selected from the group consisting of glycerol, sorbitol, and other mono and polyglycols.

In yet even another aspect, the one or more humectants comprise glycerol.

In an additional aspect, the invention encompasses a method of inhibiting plant growth which comprises applying to the plant the composition of any preceding aspect or a water-diluted formula of the composition of any preceding aspect.

Other aspects and embodiments of the invention are described herein below.

DETAILED DESCRIPTION OF THE INVENTION

As noted above, the most commonly used formulations of high strength glyphosate are IPA and K salts. The main disadvantages of IPA salt formulations are high viscosity of the solution and high flammability of IPA starting material. This creates inconvenience and potential risk during handling and manufacturing:

In contrast to IPA, DMA has a higher flash and boiling point and supplied as 40% solution. It has been found that the maximum stable fully loaded concentration for DMA glyphosate is 560 gae/L. The DMA formulation has suitable viscosity and stability, and to increase the concentration of active ingredient above 560 gae/L, the present disclosure demonstrates that a mixed salt of glyphosate can be used.

It was surprisingly found that through the incorporation of potassium along with DMA, it was possible to achieve a more concentrated glyphosate formulation of at least 580 gae/L. In addition, this formulation retains the capacity for surfactant loading for efficacious herbicidal activity in comparison to industry standard glyphosate herbicides.

The present inventors have discovered highly advantageous formulations of DMA/K. For the DMA/K combination, it was found that one particularly advantageous concentration of cations is 50% DMA and 50% K. As described herein, the percentage of the composition formulated to include potassium salt or dimethylamine salt is defined as the percentage of total glyphosate that will be in salt form with potassium or dimethylamine, respectively.

In one aspect of the invention, the DMA can be included to form salt with, for example, an amount of about 5%, about 10%, about 20%; about 25%, about 30%, about 35%, about 40%, about 43%, about 45%, about 48%, about 50%, about 53%, about 55%, about 58%, or about 60%, or greater, in weight, of total glyphosate, or about 20% to about 55%, about 40% to about 45%, about 45% to about 50%, about 45% to about 55%, about 50% to about 55%, or about 55% to about 60%, or about 65% to 70%, or about 75% to 80%, or about 85% to 90%, in weight, of total glyphosate.

In certain aspects, the remainder of glyphosate can be present in predominantly the potassium salt form. In other aspects, the potassium can be included, for example, in an amount to form a salt with about 30%, about 40%, about 42%, about 50%, about 52%, about 55%, about 57%, about 60%, about 65%, about 70%, about 75%, about 80%, about 85%, about 90%, by weight, of total glyphosate, or in an amount to form a salt with about 20% to about 95%, about 30% to about 80%, about 40% to about 45%, about 45% to about 50%, about 45% to about 55%, about 50%, to about 55%, or about 55% to about 60%, or about 65% to 70%, or about 75% to 80%, or about 85% to 90%, by weight, of total glyphosate.

In particular aspects, the combined sum of glyphosate in DMA and K salts is more than 50% of total glyphosate, for example, at least about 50%, at least about 55%, at least about 60%, at least about 65%, at least about 70%, at least about 75%, at least about 80%, at least about 85%, at least about 90%, at least about 95%, at least about 98%, or at least about 99%, of total glyphosate, or in an amount of about, 50% to about 100%, or about 60% to about 100%, about 70% to about 100%, about 75% to about 100%, about 85% to about 100%, about 90% to about 95%, about 90% to about 98%, or about 95% to about 100% of total glyphosate. Alternatively, the combined sum of glyphosate in DMA and K salts is about 5%, about 10%, about 20%, about 30%, about 40%, about 45%, about 50%, or greater of total glyphosate.

The DMA/K mixed salts of glyphosate provide certain advantages over other salts that have been commercialized. In particular, the suggested formulations provide safer options for high loaded glyphosate formulation production, produce stable, practically and economically convenient herbicide concentrates, compared to IPA formulations. The suggested formulations allow higher acid equivalent concentrations than commercially available K salts.

Furthermore, the DMA/K salts have a lower molecular weight than the IPA or MEA salts. Thus, at a given salt concentration, the DMA/K salt formulations of glyphosate have a higher glyphosate acid equivalent content than commercially available IPA or MEA salt formulations.

Thus, in one aspect, the present invention is directed to a high strength herbicidal concentrate composition comprising the DMA/K salt of glyphosate and an efficacious surfactant. More specifically, the present invention provides a high strength herbicidal concentrate composition comprising: (a) water, (b) glyphosate, predominantly in the form of the DMA/K mixed salts, in solution in the water in an amount greater than about 350 gae/L of the composition, and (c) optionally at least one surfactant.

The herbicidal formulation includes the glyphosate salt in an amount sufficient to provide the high strength formulation. In preferred embodiments, the high strength herbicidal formulation includes greater than about 350 gae/L based upon the glyphosate acid equivalent of the glyphosate salt; more preferably, the high strength herbicidal formulation includes greater than about 440 gae/L based upon the glyphosate acid equivalent of the glyphosate salt; most preferably, the high strength herbicidal formulation includes greater than about 480 gae/L based upon the glyphosate acid equivalent of the glyphosate salt.

In other aspects, the formulation includes, e.g., about 350 gae/L, about 360 gae/L, about 380 gae/L, about 400 gae/L, about 420 gae/L, about 440 gae/L, about 460 gae/L, about 480 gae/L, about 500 gae/L, about 520 gae/L, about 540 gae/L, about 560 gae/L, about 580 gae/L, or about 600 gae/L, or greater glyphosate, with upper limits based on solubility.

In yet other aspects, the formulation includes, e.g., about 350 to about 360 gae/L, about 360 to about 380 gae/L, about 380 to about 400 gae/L, about 400 to about 420 gae/L; about 420 to about 440 gae/L, about 440 to about 460 gae/L, about 460 to about 480 gae/L, about 480 to about 500, about 500 to about 520 gae/L, about 520 to about 540 gae/L, about 540 to about 560 gae/L, about 560 to about 580 gae/L, about 580 to about 600 gae/L, or greater, glyphosate. It can include a range of about 350 gae/L and greater, with upper limits based on solubility.

In preferred aspects, the present invention is directed to a high strength herbicidal formulation that is storage stable at high temperatures. That is, the formulation forms a clear, homogeneous, stable solution that does not exhibit cloudiness under the storage conditions. More preferably, the formulations of the present invention are stable at temperatures greater than or equal to about 50° C.

In addition, the high strength herbicidal formulation should not exhibit separation or precipitation (or crystallization) of any of the components at low temperatures. For example, the high strength formulation remains a clear solution at temperatures below about 10° C., about 8° C., about 6° C., about 4° C., about 2° C., or preferably at temperatures below about 0° C.

The term "predominantly" in the present disclosure means that at least 50 percent, preferably at least 75 percent, and more preferably at least 95 percent by weight of the glyphosate, expressed as acid equivalents, is present as the DMA/K salts. The balance can be made up of other salts, such as the IPA, provided that the formulation remains a clear, homogeneous liquid that is stable at temperatures at least as high as 50° C. and does not exhibit any precipitation at temperatures as low as 10° C.

For example, the amount can be at least about 50%, about 55%, about 60%, about 65%, about 70%, about 75%, about 80%, about 85%, about 90% or about 95%. DMA/K salts, or about 50 to about 55%, about 55% to about 60%, about 60 to about 65%, about 65 to about 70%; about 70 to about 75%, about 75 to about 80%, about 80 to about 85%, about 85 to about 90%, about 90 to about 95%, or preferably about 50 to about 100% DMA/K salts.

The high strength herbicidal formulation can also include a surfactant, for example, in an efficacy-enhancing amount. In preferred embodiments, the surfactant is selected to be compatible in solution with the high concentration of the glyphosate in the herbicidal formulation. By use of the term "compatible" in the present application, it will be understood by those skilled in the art to include within its meaning that the resulting solution does not exhibit a phase separation or precipitation in the formulation that can be initially observed as a cloudiness and which is typically determined at a specified temperature.

Combinations of surfactant and DMA/K salts of glyphosate can be selected to remain compatible in the formulation at high concentration. The resulting aqueous composition can be provided as a high strength herbicidal formulation. The DMA salts of glyphosate are compatible with a wide variety of surfactants. Preferred surfactants are selected from: alkyl polyglucosides, e.g., AGNIQUE PG 8107, tallow alkylamines with degree of ethoxylation no more than about 5, cationic surfactants like quaternary ammonium compounds, separately or as a mixture (e.g., from about 1:1 to about 6:1, or about 1:6 to about 6:1) used, for example, as built in systems or tank adjuvants.

Non-limiting examples of commercially available alkyl polyglucosides include, for example, AGNIQUE™, or AGRIMUL™ surfactants from Cognis Corporation, Cincinnati, Ohio; Atlox surfactants from Uniqema, New Castle, Del. 19720; or AG surfactants from AKZO NOBEL Surface Chemistry, LLC, such as: AGNIQUE PG 8105 Surfactant—an alkyl polyglucoside in which the alkyl group contains 8 to 0.10 carbon atoms and having an average degree of polymerization of 1.5; AGNIQUE PG 8166 Surfactant—an alkyl polyglucoside in which the alkyl group contains 8 to 16 carbon atoms and having an average degree of polymerization of 1.6; AGNIQUE PG 266 Surfactant—an alkyl polyglucoside in which the alkyl group contains 12 to 16 carbon atoms and having an average degree of polymerization of 1.6; AGNIQUE PG 9116 Surfactant—an alkyl polyglucoside in which the alkyl group contains 9 to 11 carbon atoms and having an average degree of polymerization of 1.6; AGNIQUE PG 264-U Surfactant—an alkyl polyglucoside in which the alkyl group contains 12 to 16 carbon atoms and having an average degree of polymerization of 1.4; AGNIQUE PG 8107 Surfactant—a $C_{8-16}$ alkyl polyglucoside in which the alkyl group contains 8 to 10 carbon atoms and having an average degree of polymerization of 1.7; AGNIQUE PG 266 Surfactant—a $C_{12-16}$ alkyl polyglucoside in which the alkyl group contains 12 to 16 carbon atoms and having an average degree of polymerization of 1.6; AL 2575/AL 535 Surfactant—a $C_{8-11}$ alkyl polyglucoside in which the alkyl group contains 8 to 11 carbon atoms and having a HLB 12-13; Akzo Nobel AG 6202, AG 6206, or AG 6210 surfactants which are 2 ethylhexyl branched $C_8$; linear hexyl $C_6$; and linear $C_8$-$C_{10}$ alkyl polyglucosides respectively. The alkyl polyglucosides may be present in the formulations of the invention in an amount of about 6 to about 12 percent by weight, based on the total weight of the composition.

In other aspects, the formulations for use in the present invention can be selected to include one or more of the following types of surfactants: alkoxylated alkylamine surfactants having 8 to 22 carbon atoms and a total of 1-20 alkylene oxide groups, available for example from Akzo Nobel as Ethomeen™ C/15, Ethomeen™ T/15, and Ethomeen™ C/12 respectively; polymeric quaternary ammonium surfactants, such as Barquat PQ-2; alkylpolyglycosides such as Akzo Nobel AG 6202 or AG 6210; or anionic ester derivatives of alkylpolyglycosides such as the Eucarol™ AGE surfactants. The surfactant may be present in the formulations of the invention in an amount of about 7 to about 15 percent weight/volume. Amounts of surfactant can be higher or lower depending on whether the surfactant is added as a substantive or auxiliary agent, in accordance with standard practice.

The surfactant can be included in the herbicidal formulation in a desired concentration. Preferably the desired concentration is sufficient to enhance the herbicidal activity of the resulting formulation over that observed with a comparable herbicidal formulation without the surfactant. More preferably, the herbicidal formulation includes the surfactant in amounts not less then 10 g/l, for example, at least about 10 g/l, about 20 g/l, about 30 g/l, about 40 g/l, about 50 g/l, about 60 g/l, about 70 g/l, about 80 about 90 g/l, about 100 g/l, about 110 g/l, about 120 g/l, about 130 g/l, about 140 g/l, about 150 g/l, about 160 g/l, about 170 g/l, about 180 g/l, about 190 g/l, about 200 g/l, or about 210 g/l, or for example, about 10 g/l to about 50 g/l, about 50 g/l to about 100 g/l, about 100 g/l to about 150 g/l, or about 150 g/l to about 210 g/l, or for example, between about 20 g/l and about 200 g/l, or between about 100 g/l and about 150 g/l.

Other adjuvants may be included in the formulations of the invention, for example, humectants, in particular, polyols (e.g., glycerol, sorbitol, etc.), as well as viscosity adjusting ingredients (e.g., propylene glycol, diethylene glycol, etc.), and pH adjusting ingredients.

It has been determined that, with selection of a specific surfactant in combination with the DMA/K salt of glyphosate, the characteristics (e.g., viscosity) of the resulting herbicidal formulation can be improved. Most preferred are mixtures of surfactants. For example, alkyl polyglucosides can improve viscosity, i.e., the viscosity of the formulation containing the blend of surfactants is significantly lower than that of formulations containing individual surfactants at the same concentration.

In preferred embodiments, the herbicidal formulation is provided to exhibit a viscosity of less than about 2500 cps, about 2000 cps, about 1000 cps, 500 cps, about 300 cps, about 200 cps, about 150 cps, or preferably less than about 100 cps or about 50 cps at around 25° C. The viscosity of the composition is expected to be no more than 2500 cps, no more than 2000 cps, no more than 1500 cps, or no more than 1000 cps, at temperatures as low as 0° C. Viscosity may be measured using any technique known to those skilled in the art, for example, using a Brookfield Synchro-lectric Model LVT Viscometer. An apparent viscosity can be measured by first stirring the sample with a glass rod for 10 seconds, placing the sample on the instrument, turning the instrument on, and measuring the value after 3 revolutions of the measuring dial. Typically the measurement is made using a #3 spindle rotating at 30 RPMs; however depending upon the viscosity of the sample, different spindles and differing rotational speeds can be utilized, as known by those skilled in the art.

In another aspect, the present invention is directed to a method of inhibiting plant growth with a herbicidal formulation. "Inhibition" of growth as used herein includes preventing, reducing, or stopping plant growth as well as killing plants and/or plant parts. The formulation can be provided as described herein. The formulation can be applied as a post-emergent or pre-emergent herbicide. The formulation can be applied as a highly concentrated solution or preferably can be diluted with water prior to application.

The formulations are preferably applied in an amount sufficient to induce an herbicidal effect. For example, a formulation prepared according the present invention can be applied as an aqueous solution to plants including the plants leaves, stems, branches, flowers, and/or fruit. The herbicidal formulation can be applied in a herbicidally effective amount sufficient to inhibit plant growth or kill individual plants.

The agricultural compositions prepared according to the present invention are highly effective as herbicide compositions against a variety of weeds. The formulations of the present invention can be used as is or combined with other components including other agriculturally acceptable adjuvants commonly used in formulated agricultural products, such as emulsifiers, penetrants, preservatives, freeze point depressants, antifreezes and evaporation inhibitors, antifoam agents, compatibilizing agents, sequestering agents, pH modifiers (buffers, acids, and bases), neutralizing agents, corrosion inhibitors, dyes, odorants, penetration aids, wetting agents, spreading agents, dispersing agents, thickening agents, pigments and/or dyes, fillers, carriers, colorants including salts such as calcium, magnesium, ammonium, potassium, sodium, and/or iron chlorides, fertilizers such as ammonium sulfate and ammonium nitrate; urea, crop oil, humectants such as polyols and mono glycols (e.g., sorbitol, glycerol, butylene glycol, sorbitol, hexylene glycol, caprylyl glycol, neopentyl glycol, ethylene glycol, propylene glycol, polyethylene glycol), and other biologically and/or agriculturally active components, and the like. The concentrated agricultural formulations can be diluted in water and then applied by conventional means well known to those in the art.

The advantages of the high strength formulations of the invention include at least the following: 1) Manufacturing process incorporates less flammable raw materials, and produces no sharp amine smell in factory; 2) Formulations show compatibility with a wide range of surfactants as compared to potassium only formulations; 3) Formulations allow use of biodegradable surfactants (e.g. alkyl polyglucosides), which are more environmentally friendly compared to amine ethoxylate surfactants used with IPA formulations; 4) Formulations require less packaging and less hazardous material for disposal; 5) Formulations show stable viscosity which does not significantly change in a wide range of temperatures, making the formulations easy to handle and transfer even in colder weather. Further advantages of the high strength formulations include easier transportation and storage, and more effective production. More final product is contained in each unit. For example, packaging of 1000 liters of a 36% solution, requires fifty 20 liter containers. In contrast, 1000 liters of a 58% solution gives the same quantity of active ingredient, but uses only thirty-one 20 liter containers. This provides clear economic benefits.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1

DMA/K Salt of Glyphosate at 560 gae/L

The vat was loaded with half of required amount of glyphosate acid. The calculated amount of DMA was based on a 40% solution. For different concentrations, the required adjustments were made. The calculated quantity of water was pumped in, and then DMA solution was pumped in at low speed. The reaction mixture was allowed to cool down, and the rest of the glyphosate acid was added. Next, the potassium hydroxide was loaded, maintaining a temperature below 50° C. This was allowed to sit until all the glyphosate was dissolved. The physical appearance of solution was checked. In the case of noticeable cloudiness, some additional potassium hydroxide was added. The remaining ingredients were added in. This was mixed. Water was added to bring to volume, and a sample was submitted for laboratory testing. The concentration of active ingredient was adjusted, if required. The calculated percentages were DMA—50% calc.; potassium—50% calc.

For 1000 ltr batch:

| INGREDIENT: | QUANTITY (kg): |
|---|---|
| Glyphosate Acid | 589.48 |
| DMA (40% sol.) (calculated as 105% extra of 50% glyphosate) | 206.28 |
| Potassium Hydroxide | 97.8 |
| AGNIQUE PG-8107 | 100 |
| Antifoam 1520-US | 1 |
| Water | To volume |

Example 2

DMA/K Salt of Glyphosate at 580 gae/L

The vat was loaded with half of required amount of glyphosate acid. The calculated amount of DMA was based on a 40% solution. For different concentrations, the required adjustments, were made. The calculated quantity of water was pumped in, and then DMA solution was pumped in at low speed. The reaction mixture was allowed to cool down, and the rest of the glyphosate acid was added. Next, the potassium hydroxide was loaded, maintaining a temperature below 50° C. This was allowed to sit until all the glyphosate was dissolved. The physical appearance of solution was checked. In the case of noticeable cloudiness, some additional potassium hydroxide was added. The remaining ingredients were added in. This was mixed. Water was added to bring to volume, and a sample was submitted for laboratory testing. The concentration of active ingredient was adjusted, if required. The calculated percentages were DMA—50% calc.; potassium—50% calc.

For 1000 ltr batch:

| INGREDIENT: | QUANTITY (kg): |
|---|---|
| Glyphosate Acid (95%) | 610.53 |
| DMA (40% sol.) (calculated as 105% of 50% glyphosate) | 213.64 |
| Potassium Hydroxide | 101.28 |
| Glycerol | 10 |
| AGNIQUE PG-8107 | 100 |
| Antifoam 1520-US | 1 |
| Water | 100 + to volume |
| Ammonium Sulphate | 12.21 |

Example 3

DMA/K Salt of Glyphosate at 500 gae/L

The vat was loaded with water and half of required amount of glyphosate acid. The calculated quantity of water was added in, and then the DMA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were DMA—50% calc.; potassium—50% calc.

For 1000 ltr batch:

| INGREDIENT: | QUANTITY (kg): |
|---|---|
| Glyphosate Acid (95%) | 526.31 |
| DMA (40% sol.) (calculated as 105% of 50% glyphosate) | 184.18 |
| Potassium Hydroxide | 87.31 |
| Glycerol | 10 |
| AGNIQUE PG-8107 | 100 |
| Antifoam 1520-US | 1 |
| Water | 100 + to volume |
| Ammonium Sulphate | 12.21 |

For all of the preceding examples, additional ingredients, including surfactants, defoamers, and humectants, were put in after reaction mixture cooled down and all ingredients had reacted. For all of the above, the formulated products showed excellent stability; pH range: 3.3-7; and density range: 1.12-1.6.

Example 4

Field Trial of DMA 580 Efficacy in Comparison to Roundup Transorb®

Introduction: The purpose of the trial was to measure the Glyphosate 580 DMA (AGNIQUE™ AGNIQUE PG-8107 surfactant) efficacy compared to Roundup Transorb® 540. The trial was conducted at Owen Chattertons Farm, Maddisons Road near Rolleston. The test crop was ryegrass and clover pasture. The trial was conducted in 55×30 cm size trays. Representative tray size pasture samples of 7.5 cm depth were sliced from Owen Chatterton's Weedons Farm, Canterbury, New Zealand.

Sprayer Calibration:

Before spraying, trays were placed randomly in rows to facilitate precise and even active ingredient distribution. Spray width was 1.5 m with Donaghys "PET Bottle Hand sprayer". Spraying was calibrated to deliver 150 mL in 3.5 seconds over a spray run of 5 m.

Treatments:

Following four treatments were applied in duplicate.

| Treatment | Herbicide L per hectare equivalent | Herbicide mL per 7.5 m$^2$ in 150 ml water |
|---|---|---|
| Roundup Transorb (540) | 2.67 | 2.00 |
| Glyphosate 580 DMA | 2.48 | 1.86 |

Results:

Grass in both treatments showed a similar degree of yellowness for both treatments at 15 days after treatment.

All publications and patents mentioned in the above specification are herein incorporated by reference. Any discussion of the publications and patents throughout the specification should in no way be considered as an admission that such constitute prior art, or widely known or common general knowledge in the field.

Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the scope of the invention. The invention illustratively described herein may be practiced in the absence of any element or elements, or limitation or limitations, which are not specifically disclosed herein as essential.

In addition, in each instance herein, in embodiments or examples of the present invention, the terms 'comprising', 'including', etc. are to be read expansively without limitation. Thus, unless the context clearly requires otherwise, throughout the description and the claims, the words 'comprise', 'comprising' and the like are to be construed in an inclusive sense as opposed to an exclusive or exhaustive sense; that is to say in the sense of "including but not limited to".

What is claimed is:

1. A stable high strength herbicidal composition consisting essentially of: (a) water; (b) glyphosate, predominantly in the form of a combination of dimethylamine salt and potassium salt, in solution in the water in an amount of about 540 grams or greater of acid equivalent per liter of the composition, wherein the composition is formulated to include dimethylamine in an amount to form a salt with about 5% or greater, by weight, of total glyphosate and to include potassium in an amount to form a salt with about 20% or greater, by weight of total glyphosate, and wherein the combined sum of glyphosate in dimethylamine and potassium salts is at least 45% of total glyphosate.

2. The composition of claim 1, wherein the composition is formulated to include dimethylamine in an amount to form a salt with about 20% to about 55% by weight, of total glyphosate and to include potassium in an amount to form a salt with a percentage of total glyphosate so that the combined sum of glyphosate in dimethylamine and potassium salts is at least 45% of total glyphosate.

3. The composition of claim 1, wherein the composition is formulated to include dimethylamine in an amount to form a salt with about 50%, by weight, of total glyphosate and to include potassium in an amount to form a salt with a percentage of total glyphosate so that the combined sum of glyphosate in dimethylamine and potassium salts is at least 50% of total glyphosate.

4. The composition of claim 1, wherein the composition is formulated to include potassium in an amount to form a salt with about 20% to about 95%, by weight, of total glyphosate.

5. The composition of claim 2, wherein the composition is formulated to include potassium in an amount to form a salt with about 30% to about 80%, by weight, of total glyphosate.

6. The composition of claim 1, wherein the composition is formulated to include potassium in an amount to form a salt with about 50%, by weight, of total glyphosate.

7. The composition of claim 1, which comprises greater than or about 560 grams of acid equivalent of glyphosate per liter of the composition.

8. The composition of claim 1 further including one or more surfactants and/or one or more humectants.

9. The composition of claim 8, wherein the one or more surfactants are selected from the group consisting of alkyl polyglucosides and polymeric quaternary ammonium compounds.

10. The composition of claim 8, wherein the one or more surfactants comprise an alkyl polyglucoside.

11. The composition of claim 8, wherein the one or more surfactants comprise a mixture of alkyl polyglucoside and polymeric ammonium quaternary compound in a ratio of about 1:9 to about 9:1.

12. The composition of claim 8, wherein the one or more humectants are selected from the group consisting of glycerol, sorbitol, and other mono and polyglycols.

13. The composition of claim 8, wherein the one or more humectants comprise glycerol.

14. A method of inhibiting plant growth which comprises applying to a plant the composition of claim 1.

15. A method of inhibiting plant growth which comprises applying to a plant a water-diluted formula of the composition of claim 1.

16. The composition of claim 1 which comprises greater than or about 580 grams of acid equivalent of glyphosate per liter of the composition.

17. The composition of claim 1, wherein the viscosity of the high strength herbicidal composition is less than about 2500 cps at 0° C.

18. A stable high strength herbicidal composition consisting essentially of: (a) water; (b) glyphosate, predominantly in the form of a combination of dimethylamine salt and potassium salt, in solution in the water in an amount of about 540 grams or greater of acid equivalent per liter of the composition, wherein the composition is formulated to include dimethylamine in an amount to form a salt with about 5% or greater, by weight, of total glyphosate and to include potassium in an amount to form a salt with about 20% or greater, by weight of total glyphosate, wherein the combined sum of glyphosate in dimethylamine and potassium salts is at least 45% of total glyphosate; and (c) optionally one or more surfactants, and/or one or more humectants; and wherein the viscosity of the high strength herbicidal composition is no more than 2500 cps at 0° C.

* * * * *